United States Patent [19]
Koczab

[11] Patent Number: 5,879,344
[45] Date of Patent: *Mar. 9, 1999

[54] COMPOSITE NONWOVEN MATERIAL AND ITS APPLICATION TO ANY ABSORBENT ARTICLE OF HYGIENE

[75] Inventor: Jean-Pierre Koczab, Bondues, France

[73] Assignee: Peadouce, Linselles, France

[*] Notice: The term of this patent shall not extend beyond the expiration date of Pat. No. 5,556,392.

[21] Appl. No.: 686,642

[22] Filed: Jul. 26, 1996

Related U.S. Application Data

[63] Continuation of Ser. No. 436,223, May 17, 1995, Pat. No. 5,556,392.

[30] Foreign Application Priority Data

Nov. 20, 1992 [FR] France .................. 92 13998

[51] Int. Cl.⁶ .................................................. A61F 13/15
[52] U.S. Cl. .................... 604/383; 604/378; 442/402; 442/403
[58] Field of Search .................. 604/383, 369, 604/370, 378; 442/402–408

[56] References Cited

U.S. PATENT DOCUMENTS

| | | |
|---|---|---|
| 3,206,351 | 9/1965 | Smith . |
| 3,545,442 | 12/1970 | Wicker et al. . |
| 4,223,677 | 9/1980 | Anderson . |
| 4,985,279 | 1/1991 | Mussallem, III . |
| 5,169,712 | 12/1992 | Tapp . |
| 5,368,909 | 11/1994 | Langdon et al. . |
| 5,470,326 | 11/1995 | Dabi et al. . |

FOREIGN PATENT DOCUMENTS

| | | |
|---|---|---|
| 0151018A3 | 8/1985 | European Pat. Off. . |
| 0232729A1 | 8/1987 | European Pat. Off. . |
| 0252041A3 | 1/1988 | European Pat. Off. . |
| 0306262A1 | 3/1989 | European Pat. Off. . |
| 0313800A1 | 5/1989 | European Pat. Off. . |
| 0352208A1 | 1/1990 | European Pat. Off. . |
| 2169348 | 7/1973 | France . |
| 3029315 | 8/1991 | Germany . |
| WO 91/11164 | 8/1991 | WIPO . |

*Primary Examiner*—John G. Weiss
*Assistant Examiner*—Dennis Ruhl
*Attorney, Agent, or Firm*—Burns, Doane, Swecker & Mathis, L.L.P.

[57] ABSTRACT

A composite nonwoven material includes a layer made of a nonwoven material which is permeable to body fluids and a sheet of carded synthetic fibers permeable to body fluids. The carded fiber sheet is bonded to the nonwoven layer solely by needling. An absorbent article of hygiene also includes the composite nonwoven material.

13 Claims, 4 Drawing Sheets

COMPOSITE NONWOVEN MATERIAL AND ITS APPLICATION TO ANY ABSORBENT ARTICLE OF HYGIENE

CROSS-REFERENCE TO RELATED APPLICATIONS

The present application is a continuation application of U.S. patent application Ser. No. 08/436,223, filed on May 17, 1995 now U.S. Pat. No. 5,556,392.

BACKGROUND OF THE INVENTION

1. Field of the Invention

The invention relates generally to a new nonwoven material which, when employed as a surface web or sheet or in addition to the surface web as a strip in the crotch region in an absorbent article of hygiene, such as a diaper or dressing for an incontinent person, permits a better isolation of the user's skin from the absorbent part of the article of hygiene.

2. Discussion of Related Art

Absorbent articles of hygiene such as diapers and dressings for incontinent persons generally comprise an outer layer made of material which is impervious to body fluids, a pad or mat of absorbent material and a surface web or sheet which is permeable to body fluids such as urine, of size and shape which are similar to those of the impervious outer layer of the article. This surface web which is permeable to body fluids is intended to isolate the skin from the moistened absorbent pad. Consequently, the surface web must have a suitable degree of softness and must ensure a desired isolation between the skin and the absorbent pad. The function of the absorbent pad is to absorb the fluids and consequently it must have a high rate of absorption as well as a high absorption capacity. A particularly effective absorbent pad is described in document EP-A-0,232,729. This absorbent pad or mat is made up of a sheet of long absorbent fibers lined on its faces with a layer of cellulose wadding. The sheet lined with the layers of wadding is needled from both faces.

A particularly effective mat described in this Patent Application EP-A-0,232,729 comprises two sheets of long fibers, a first sheet of absorbent fibers and a second sheet of nonabsorbent fibers, between which particles of superabsorbent material are arranged, the sheet of nonabsorbent fibers being lined externally with a layer of nonwoven and the sheet of absorbent fibers being lined externally with a layer of cellulose wadding. The whole is bonded by needling from both faces.

In absorbent articles of hygiene such absorbent mats or pads are covered with a surface web generally made of nonwoven material, the purpose of which is to isolate the skin from the absorbent pad and which must ensure a pleasant contact with the skin and the desired isolation with the absorbent pad. These surface webs or sheets must exhibit, as essential properties, a pleasant contact with the skin, a high rate of passage by the body fluids and must form a barrier against rewetting.

Document FR-A-2,588,285 describes a multilayer nonwoven textile which has at least two layers of nonwoven web, one of the layers consisting of fibers of bilobed cross-section and the other layer consisting of fibers of trilobed cross-section. Each web layer is preferably obtained by the spin-bonding technique and the two web layers are joined to form the multilayer nonwoven by heat bonding in compacted and noncontinuous regions.

Document WO 87/07,117 describes an absorbent article of hygiene comprising an absorbent body surrounded by a cover. This cover or surface web consists of two layers made of nonwoven material. The first layer of nonwoven material, in contact with the user's skin, consists of a thin layer of spin-bonded fibrous tissue made of a hydrophobic material, and the second layer in contact with the absorbent body is a hydrophobic fibrous layer of fiber tissue, which is melt-bonded, similar in construction to the first layer. These two layers of surface web are not joined together in the region intended to come into contact with the user's body.

Document WO 88/05,269 relates to a surface web for a disposable absorbent article made up of at least two layers of nonwoven, which may be identical or different and which are joined by lines of adhesive forming an open pattern.

OBJECTS AND SUMMARY

An aim of the present invention is therefore to provide a composite nonwoven material which has a desired degree of softness, an improved rate of passage by the liquids and improved resistance to rewetting.

Another aim of the present invention is to provide an absorbent article of hygiene such as diapers and dressings for incontinent persons, comprising a surface web made of such a composite nonwoven material.

Another aim of the present invention is to provide an absorbent article of hygiene such as diapers and dressings for incontinent persons, comprising, in addition to a surface web made of conventional nonwoven material, a strip in the crotch region which is made of the composite nonwoven material according to the invention.

According to the present invention a composite nonwoven material is produced, which comprises at least one first layer consisting of a nonwoven material and, on this first layer, a sheet of fibers of carded type, the sheet of fibers of carded type being bonded to the base layer by needling.

In another embodiment of the present invention the composite nonwoven material comprises a first layer made of a nonwoven material, a sheet of fibers of carded type and a second layer made of a nonwoven material of lower weight per unit area than the first layer of nonwoven material, the sheet of fibers of carded type being arranged between the first and the second layers of nonwoven material, the whole being bonded by needling.

The composite material according to the invention has a time of break-through by the body fluids which is shorter and a degree of isolation which is better than the previous nonwovens employed hitherto for making the surface webs and crotch region strip of absorbent articles of hygiene.

According to the present invention an absorbent article of hygiene such as a diaper is also produced, which comprises an outer layer made of impervious material, an absorbent mat and, on this absorbent mat, a surface web consisting of the composite material according to the invention. When the surface web consists of the composite material according to the invention comprising a nonwoven layer and the sheet of fibers of carded type, the sheet of carded type forms the outermost layer of the web, that is to say the layer directly in contact with the absorbent pad, whereas the nonwoven layer forms the innermost layer of the surface web, which will be in contact with the user's body. When the surface web consists of the composite material according to the invention comprising a carded sheet of fibers between two nonwoven layers, the nonwoven layer of lower weight per unit area forms the outermost layer of the surface web, that is to say the layer directly in contact with the absorbent pad, and the nonwoven layer of higher weight per unit area forms the innermost layer of the web, which will be directly in contact with the user's body.

The invention also provides an absorbent article of hygiene such as a diaper, which comprises an outer layer made of material which is impervious to body fluids, an absorbent mat, a surface web made of nonwoven material and a strip in the crotch region, consisting of the composite material according to the invention. The strip in the crotch region may be arranged either on the surface web made of conventional nonwoven material or between this web made of conventional nonwoven material and the absorbent pad. As previously described, when the composite material according to the invention is employed, consisting of a nonwoven layer and of the sheet of fibers of carded type, this sheet of fibers of carded type will form the outermost layer of the crotch region strip, whereas the nonwoven layer will form the innermost layer of the crotch region strip. Similarly, in the case where the crotch region strip consists of the composite material according to the invention, comprising a sheet of fibers of carded type included between two nonwoven layers, the nonwoven layer of lower weight per unit area will form the outermost layer of the crotch region strip, whereas the nonwoven layer of higher weight per unit area will form the innermost layer of this strip.

BRIEF DESCRIPTION OF THE DRAWINGS

The description which follows refers to the attached figures, which show, respectively.

DETAILED DESCRIPTION OF THE PREFERRED EMBODIMENTS

Figure 1:
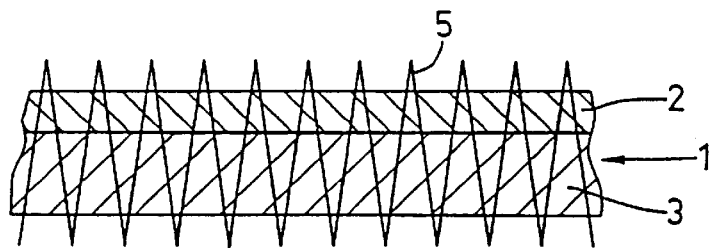
FIG. 1, a first embodiment of the composite nonwoven material according to the invention.

With reference to FIG. 1, a first embodiment of the composite nonwoven material 1 according to the invention is shown. This material comprises a first layer 2 made of a nonwoven material permeable to body fluids such as urine, and on this first layer made of nonwoven material, a sheet of fibers of carded type 3, forming a mat, permeable to body fluids, the sheet of fibers of carded type being bonded to the first layer made of nonwoven material by a needling 5 from both faces.

All types of conventional nonwoven materials, for example made of natural or synthetic textile fibers such as cellulose, viscose, polyester, polyethylene, polypropylene, nylon or ethylene-propylene copolymer fibers can be employed for the first layer made of nonwoven material. In addition, the first nonwoven layer 2 may be made of fibers of one kind or of different kinds of fibers. Also, this nonwoven layer may consist of fibers of the same denier or of different deniers. This first nonwoven layer may consist of a nonwoven material manufactured by any conventional process such as, for example, spin bonding, heat bonding, chemical bonding, bonding air blowing and spin lacing. This first nonwoven layer 2 preferably has a weight per unit area of between 10 and 30 $g/m^2$.

The sheet of fibers of carded type 3, permeable to the fluids, may consist of synthetic textile fibers such as polyester, polyethylene, polypropylene, nylon or ethylene-propylene copolymers. Polyester fibers are very particularly recommended for their resilience and comfort characteristics. It is also possible to employ profiled fibers, for example bi- or trilobed fibers. The use of such fibers makes possible the transport or diffusion of the fluids owing to their own shape. The sheet of fibers of carded type may consist of fibers of the same kind or of a mixture of fibers as a function of the type of barrier which is desired. Similarly, the sheet of fibers of carded type 3 may consist of fibers of identical or different deniers (measurement of the thickness of diameter of the fibers), the denier of the fibers of this sheet being generally between 3 and 13. In general, the sheet of fibers of carded type has a weight per unit area of between 20 and 60 $g/m^2$. The sheet of fibers of carded type 3 is obtained by well-known carding or pseudocarding techniques.

The first layer of nonwoven 2 and the layer of fibers of carded type 3 are preferably bonded by needling from both faces of the composite. Obviously, the needling density and the choice of the denier of the fibers determine the bulk (thickness of the nonwoven material). A needling density of 10 to 100 needle strokes per $cm^2$ and per face is generally employed. A single-stroke or double-stroke needling process may be employed for the needling. The composite nonwoven material obtained generally has a density of between 50 and 300 $kg/m^3$ and the layer of sheet of fibers of carded type 3 generally has a thickness greater than that of the first nonwoven layer 2.

Figure 2:
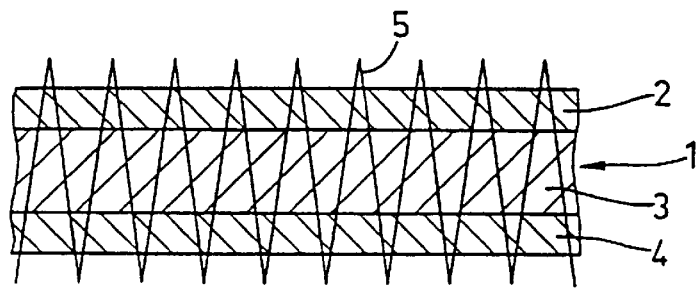
FIG. 2, a second embodiment of the composite nonwoven material according to the invention.

With reference now to FIG. 2, another embodiment of a multilayer nonwoven material according to the present invention is shown. The material comprises a first nonwoven layer 2 similar to the nonwoven layer 2 of the embodiment of FIG. 1. On this first nonwoven layer 2 there is a sheet of fibers of carded type 3, also similar to the sheet of fibers of carded type of FIG. 1. On the upper surface of the sheet of fibers of carded type 3 there is a second nonwoven layer 4. This second nonwoven layer 4 is similar to the first nonwoven layer 2 except insofar as weight per unit area is concerned. This second nonwoven layer preferably has a weight per unit area which is lower than that of the first nonwoven layer 2, and preferably lower than 20 $g/m^2$, for example 17 $g/m^2$, and, better still, lower than or equal to 15 $g/m^2$. As in the case of the composite nonwoven material of FIG. 1, the layers of the composite nonwoven material of FIG. 2 are joined by needling in the same way.

The composite nonwoven materials according to the invention are found to be particularly useful as surface webs or crotch region strip in absorbent articles of hygiene such as diapers or dressings for incontinent persons.

Figure 3:
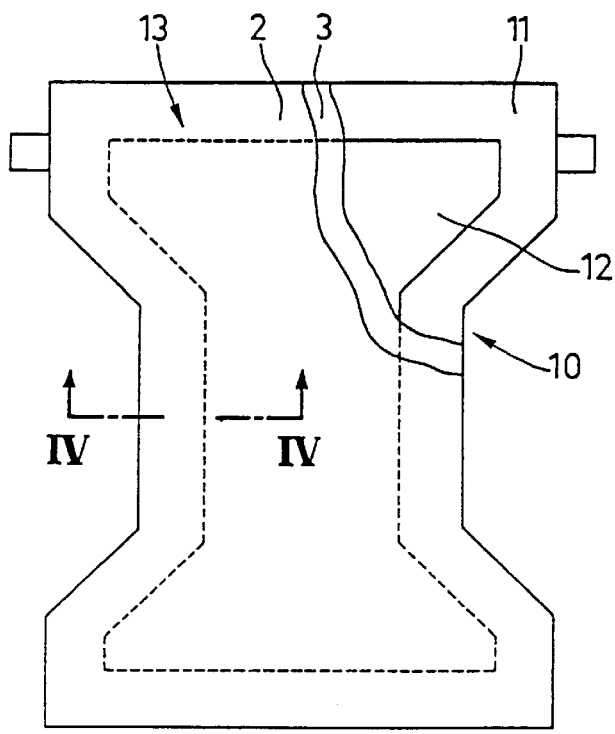
FIG. 3, a top view, with partial cutaway, of an absorbent article of hygiene such as a diaper, comprising a surface web consisting of the composite material of FIG. 1.
Figure 4:
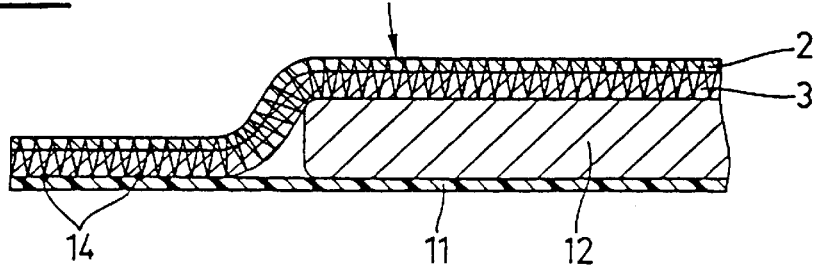
FIG. 4, a view in section along the line IV—IV of FIG. 3.

With reference to FIGS. 3 and 4, an absorbent article of hygiene 10, such as a diaper, is shown, comprising an outer layer 11 made of a flexible material impervious to body fluids, to which there is secured an absorbent mat or pad 12 which is permeable to body fluids, smaller in size than the outer layer. The absorbent pad 12 is secured to the impervious layer 11 by any conventional means such as by adhesive bonding. On this absorbent pad 12 there is a surface web 13 which is permeable to body fluids, of a size similar to that of the outer layer 11. The surface web 13 is bonded on the periphery of the absorbent pad 12 to the outer layer 11 by any means such as by adhesive bonding. As is well known in the art, the outer layer 11, the absorbent mat 12 and the surface web 13 have the shape of an hourglass comprising two relatively wide opposite end parts joined by a narrower part or crotch region. As shown in FIGS. 3 and 4, the surface web consists of the composite nonwoven material which is shown in FIG. 1 and which comprises a first nonwoven layer 2 and a sheet of fibers of carded type 3. As shown in the figures, the sheet of carded type 3 is placed directly above the absorbent pad, whereas the nonwoven layer 2 forms the innermost layer of the web intended to come into contact with the user's body.

Figure 5:
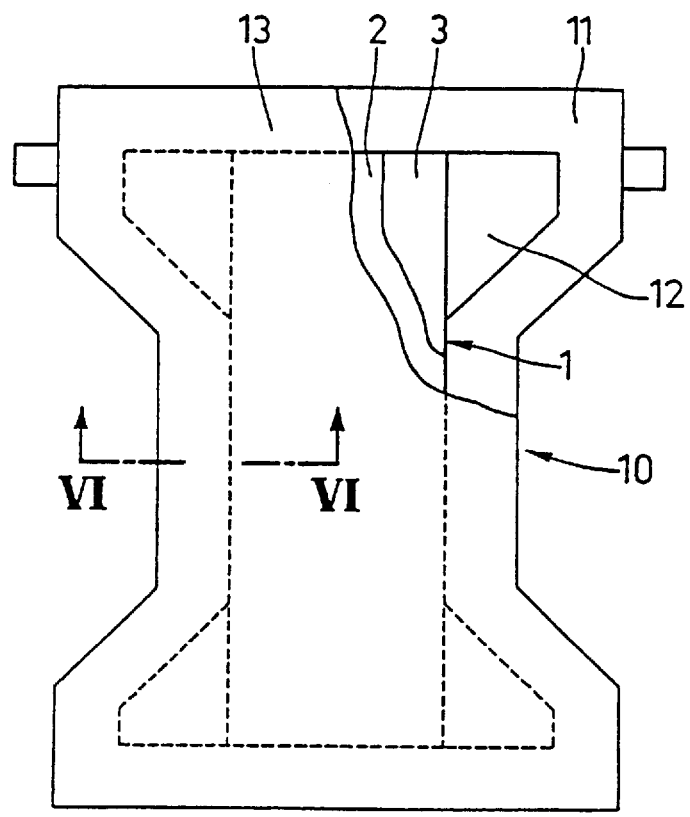
FIG. 5, a top view, with partial cutaway, of an absorbent article of hygiene such as a diaper, comprising a crotch region strip consisting of the composite material of FIG. 1.
Figure 6:
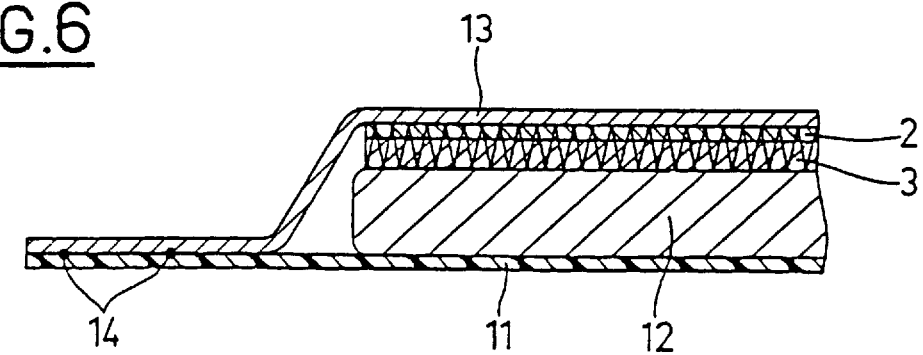
FIG. 6, a view in section along the line VI—VI of FIG. 5.

When employed in addition to a conventional surface web, the composite material according to the invention is preferably employed in the form of a crotch region strip which has a width similar to that of the crotch region of the pad and a length similar to that of this pad. In this embodiment the crotch region strip consisting of the material according to the invention is arranged either above the conventional surface web or between this conventional surface web and the pad. Such a crotch region strip consisting of the composite material shown in FIG. 1 is shown in FIGS. 5 and 6. In this embodiment the absorbent article of hygiene such as a diaper comprises an outer layer made of a material which is impervious to body fluids 11, an absorbent pad 12 secured to the outer layer 11, for example by adhesive bonding, a crotch region strip made of material according to the embodiment of FIG. 1 and a surface web 13 made of conventional nonwoven material. The surface web is joined to the impervious outer layer 11 by any conventional means such as by lines of adhesive bonding 14. As shown in the figures, the crotch region strip consisting of the material of FIG. 1 is arranged between the absorbent pad 12 and the surface web made of conventional nonwoven material 13. In this embodiment the sheet of fibers of carded type 3 of the composite material 1 is arranged directly on the inner surface of the pad 12, whereas the nonwoven layer 2 forms the innermost layer of the crotch region strip which is found to be in contact with the outer surface of the surface web made of conventional nonwoven material 13. The crotch region strip is joined to the outer surface of the web made of conventional nonwoven material 13 or to the inner surface of the absorbent pad 12 by any conventional means such as by adhesive bonding, heat-sealing, ultrasonic sealing or by needling. As indicated above, this crotch region strip made of composite material according to the invention may be arranged either on the inner surface of the surface web made of conventional nonwoven material 13 or between this surface web 13 and the absorbent pad 12. However, in all cases the nonwoven layer 2 of the composite material must form the innermost layer of the crotch region strip.

An absorbent article of hygiene according to the invention is thus produced, which has improved properties of softness, rate of passage of the body fluids and rewetting barrier.

Figure 7:
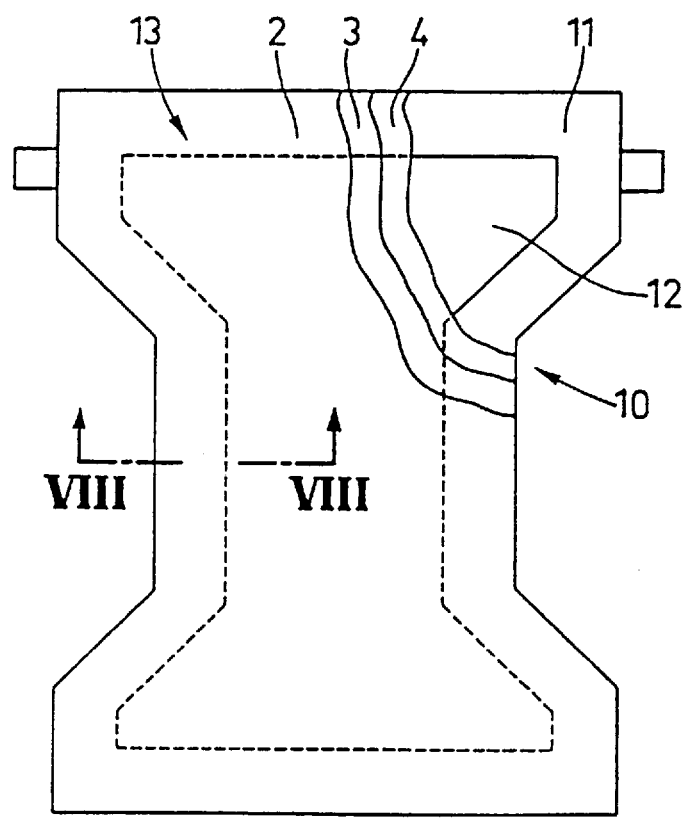
FIG. 7 a top view, with partial cutaway, of an absorbent article of hygiene such as a diaper, comprising a surface web made of composite nonwoven material according to FIG. 2.
Figure 8:
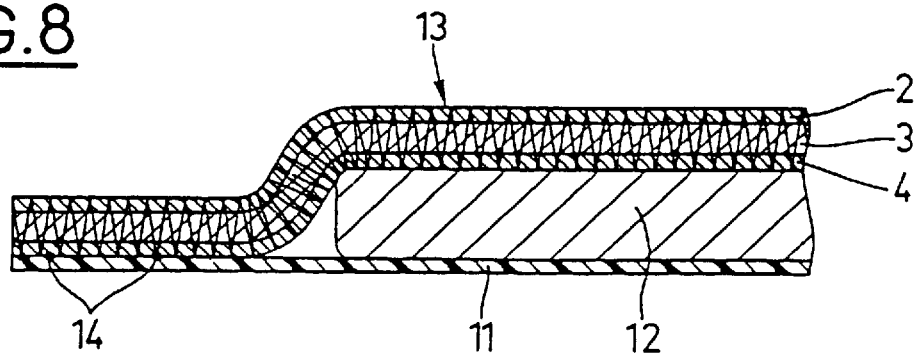
FIG. 8, a view in section along the line VIII—VIII of FIG. 7.

With reference to FIGS. 7 and 8, an absorbent article of hygiene such as a diaper is shown, comprising a surface web consisting of a composite material according to the invention as shown in FIG. 2. As above, the absorbent article of hygiene comprises an outer layer 11 made of material which is impervious to body fluids, an absorbent pad 12 and a surface web 13 consisting of the composite material according to the invention described in connection with FIG. 2. The impervious outer layer 11, the pad 12 and the surface web 13 have a shape similar to that described in connection with FIGS. 3 and 4. In this case the surface web is arranged so that the nonwoven layer 4 of lowest weight per unit area forms the outermost layer of the surface web 13, whereas the nonwoven layer 2 of highest weight per unit area will form the innermost layer of the surface web 13 intended to come into contact with the user's body.

Figure 9:
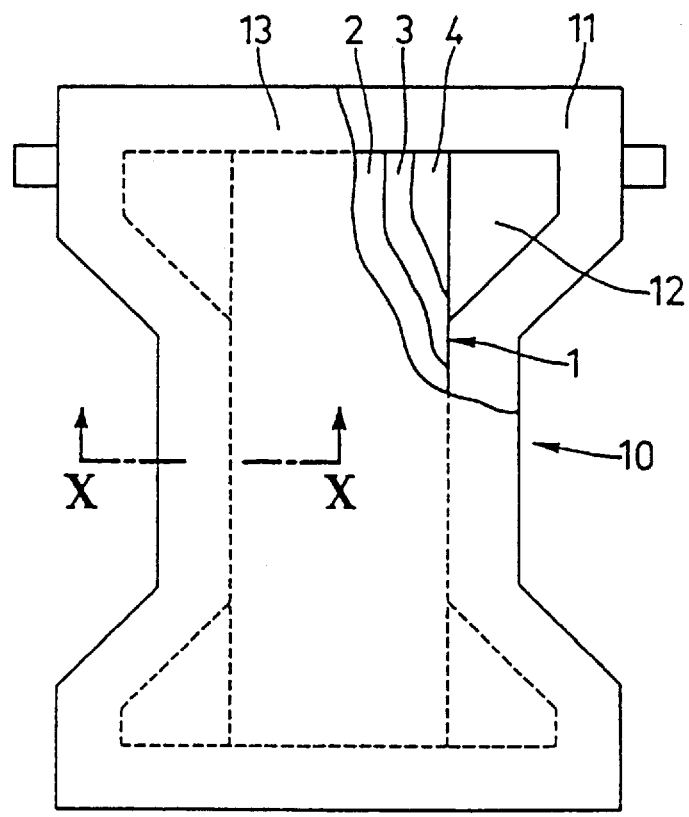
FIG. 9, a top view, with partial cutaway, of an absorbent article of hygiene such as a diaper, comprising a crotch region strip consisting of the composite nonwoven material of FIG. 2.
Figure 10:
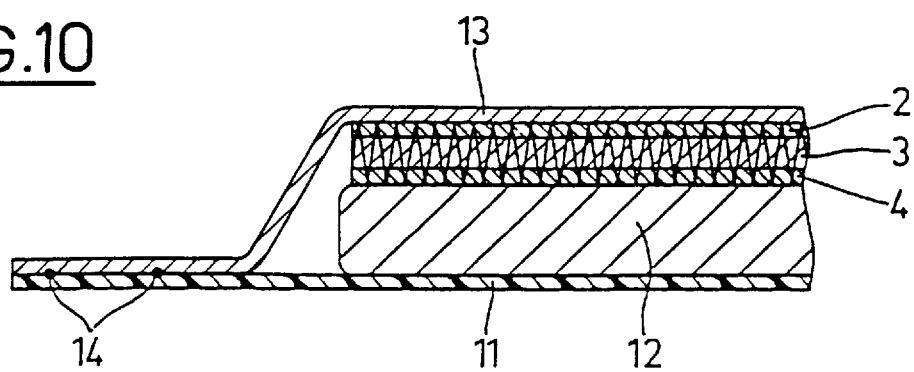
FIG. 10, a view in section along the line X—X of FIG. 9.

With reference now to FIGS. 9 and 10, an absorbent article of hygiene such as a diaper 10 is shown, similar to the absorbent of hygiene shown in FIGS. 5 and 6 and comprising, in addition to a conventional surface web 13, a crotch region strip consisting of the composite material according to the invention, described in connection with FIG. 2. The diaper 10 comprises an outer layer 11 which is impervious to body fluids, an absorbent pad 12, a crotch region strip of width similar to the width of the crotch region of the pad and of length similar to that of this pad and a surface web 13 made of conventional nonwoven material. The pad 12 is secured to the outer layer 11 by any conventional means, for example by adhesive bonding, and the surface web 13 made of conventional nonwoven material is bonded to the outer layer 11 on the periphery of the absorbent pad 12 by any conventional means such as by lines of adhesive bonding 14. The crotch region strip which, in the embodiment shown, is arranged between the pad 12 and the conventional surface web 13 is made up, as described above, of two nonwoven layers 4 and 2 between which there is the sheet of fibers of carded type 3. The nonwoven layer 4 of lower weight per unit area is situated directly on the inner surface of the pad 12, whereas the nonwoven layer 2 of higher weight per unit area forms the innermost layer of the crotch strip which is in contact with the inner surface of the web 13 made of conventional nonwoven material. The crotch region strip made of composite material according to the invention may be bonded to the absorbent pad 12 by any known means such as by adhesive bonding, heat-sealing, ultrasonic sealing or by needling, the use of the nonwoven layer 4 of lower weight per unit area allowing the absorbent pad 12 to be better secured. Obviously, as above, the crotch region strip made of composite material according to the invention could be arranged on the inner surface of the web 13 made of conventional nonwoven material, and, in this case, the nonwoven layer 4 of lower weight per unit area will form the outermost layer of the crotch region strip which will be bonded to the inner surface of the conventional surface web 13, whereas the nonwoven layer of higher weight per unit area will form the innermost layer of the crotch region strip intended to come into contact with the user's body.

An absorbent article of hygiene has thus been produced which has improved properties of softness, rate of passage of the body fluids and of rewetting barrier.

The following nonlimiting examples demonstrate the advantages obtained by employing the composite material according to the invention as surface web in diapers.

COMPARATIVE EXAMPLE A

A determination was made of the speed of break-through and the rewetting resistance of a commercial diaper (Peaudouce Action Girl® corresponding to the 8–18 kg size, of total weight 59 g, this absorbent pad having a weight of 48 g including 4.6 g of superabsorbent material) and which comprises a conventional surface web made of nonwoven polypropylene fibers (spin-bonded type) which has a weight per unit area of 20 g/m$^2$. The results of the tests are given in Table 1.

COMPARATIVE EXAMPLE B

A determination was made of the speed of break-through and the rewetting resistance of another commercial diaper, identical in size to that of comparative Example A and comprising a surface web consisting of a base layer made of nonwoven polypropylene fibers of spin-bonded type which has a weight per unit area of 30 g/m² and a crotch region strip made of nonwoven predominantly polyester fibers of air-through-bonded type which has a weight per unit area of 52 g/m², that is a total weight per unit area of 82 g/m². The results of the tests are given in Table 1.

COMPARATIVE EXAMPLE C

The surface web of the diaper of Comparative Example A was replaced with the surface web of the diaper of Comparative Example B and the speed of break-through and the rewetting resistance of the article thus obtained were measured. The results are given in Table 1.

COMPARATIVE EXAMPLE D

The crotch region strip of the diaper of Comparative Example B, that is to say the strip made of nonwoven material of air-through-bonded type which has a weight per unit area of 52 g/m², was added to the surface web of the diaper of Comparative Example A, and the speed of break-through and wetting resistance were measured. The results are given in Table 1.

COMPARATIVE EXAMPLE E

Four layers of a nonwoven material of polypropylene fibers of the spin-bonded type, each with a weight per unit area of 20 g/m² were added to the surface web of the diaper of Comparative Example A. The speed of breakthrough and the rewetting resistance of the article obtained were measured. The results are given in Table 1.

EXAMPLE 1

The surface web of the diaper of Comparative Example. A was replaced with a surface web consisting of a composite material according to the invention. In this example the composite material according to the invention consisted of a first layer of a nonwoven material of polyethylene fibers of spin-bonded type with a weight per unit area of 20 g/m² from the Corovin company, bonded by needling to a sheet of polyester fibers of carded type of 6.6 deniers which had a weight per unit area of 50 g/m², that is a total weight per unit area of 70 g/m². The needling density was 20 needle strokes per cm² and per face and the density of the material obtained was 150 kg/m³. The sheet of polyester fibers of carded type was arranged directly on the absorbent pad. The speed of break-through and the rewetting resistance of the article obtained were measured. The results are given in Table 1.

EXAMPLE 2

The surface web of the diaper of Comparative Example B was replaced with a web made of composite nonwoven material according to the invention, identical with that of Example 1, in which the sheet of fibers of carded type is then situated directly in contact with the absorbent pad of the diaper. The speed of break-through and the rewetting resistance of the article obtained were measured. The results are given in Table 1.

EXAMPLE 3

The nonwoven strip of 52 g/m² of the diaper of Comparative Example B is withdrawn and replaced with the composite nonwoven material of Example 1, with the layer of fibers of carded type in contact with the base layer made of nonwoven material of 30 g/m² of the initial surface web of the diaper. The speed of break-through and the rewetting resistance of the article obtained were measured. The results are given in Table 1.

EXAMPLE 4

To the surface web of the diaper of Comparative Example A was added a web consisting of a composite nonwoven material according to the invention comprising a first layer of a nonwoven material of polyethylene fibers of spun-bonded type of 20 g/m², a sheet of polyester fibers of carded type of 50 g/m², similar to those of Example 1, and a second layer of a nonwoven material of polypropylene fibers of spun-bonded type of 17 g/m², the three layers being bonded by needling. The needling density was 20 needle strokes per cm² and per face. The composite nonwoven material according to the invention is arranged with the second nonwoven layer in contact with the initial surface web. The speed of break-through and the rewetting resistance of the article obtained were measured. The results are given in Table 1.

TABLE 1

|  | Comparative Example A | Comparative Example B | Comparative Example C | Comparative Example D | Comparative Example E | Example 1 | Example 2 | Example 3 | Example 4 |
| --- | --- | --- | --- | --- | --- | --- | --- | --- | --- |
| 1st break-through time (s) | 67 | 57 | 50 | 44 | 246 | 47 | 48 | 40 | 35 |
| 2nd break-through time (s) | 209 | 173 | 74 | 80 | 498 | 73 | 92 | 109 | 62 |
| 3rd break-through time (s) | 225 | 249 | 204 | 118 | 424 | 80 | 120 | 220 | 68 |
| Rewetting resistance (g) | | | | | | | | | |
| after 20 minutes | 2.95 | 0.32 | 0.12 | 0.23 | 0.17 | 0.20 | 0.23 | 0.38 | 0.30 |
| after 40 minutes | 33.46 | 2.70 | 4.71 | 8.50 | 15.00 | 1.93 | 0.30 | 0.63 | 0.45 |
| after 60 minutes | 56.17 | 14.00 | 30.00 | 31.60 | 49.00 | 16.00 | 5.20 | 1.03 | 11.00 |

The break-through times and the rewetting resistance were determined as follows:

The finished products are conditioned at 23° C. and 50% relative humidity for 24 hours before the tests.

A 7×7 cm sheet of Plexiglas® perforated in its center is placed in the center of the surface web of the tested article. 100 cm³ of a saline solution containing 9 g/l of sodium chloride in distilled water is poured into the orifice in the sheet by means of a separating funnel, the flow of the funnel being adjusted so as to have a constant high level in the sheet orifice. The time elapsed between the beginning of the introduction of the saline solution and the moment at which the saline solution has disappeared into the article is measured. The measured time constitutes the first break-through time.

Six Dimar ED 939® filter papers cut into 10.2×10.2 cm squares are then weighed. A 10.2×10.2 cm 3.5 kg weight is then placed for 10 minutes on the surface web of the tested article, after the perforated sheet has been taken off. Once 10 minutes have elapsed, the six filter papers are placed under the weight and are left for another 10 minutes. At the end of this period the weight and the filter papers are removed. The filter papers are weighed. The difference in weight, in grams, between the first and second weighing gives a measure of the rewetting resistance after 20 minutes.

The above procedure is restarted twice with the same article, 24 filters being used after the second addition of saline solution and 30 filters after the third addition, respectively. The second and third break-through times and the rewetting resistance after 40 and 60 minutes are thus obtained.

As is clearly shown by the examples of Table 1 above, the use of the surface web made of composite nonwoven according to the invention as a replacement for or in addition to a conventional surface web results in a particularly advantageous combination of a short break-through time and better rewetting resistance. In particular, Example 1 shows a break-through time in the third test which is approximately 60% shorter than that of Comparative Example C and an improvement in the rewetting resistance after 60 minutes of approximately 47%.

A comparison of the results obtained in the case of Example 2 with those of Comparative Example B shows that by substituting a surface web according to the invention for the initial surface web an improvement of approximately 50% in the second and third break-through times and of approximately 63% in the rewetting resistance after 60 minutes are obtained.

Comparison of the results obtained in Example 4 with those of Example 1 shows that the use of a composite nonwoven according to the invention comprising a second nonwoven layer in addition to the conventional surface web does not harm the break-through time, while improving the rewetting resistance after 60 minutes by approximately 30%.

Finally, a comparison of the examples according to the invention with Comparative Example E shows that the total weight per unit area of the surface web does not affect the results. Thus, it may be considered that the surface web of Example 4 consists of four layers with a total weight per unit area of 107 g/m² and the surface web of Comparative Example E of five layers with a total weight per unit area of 100 g/m². Comparison of the results obtained showing, in the case of the comparative example, an increase of 500 to 600% in the break-through times and a deterioration of 345% in the rewetting resistance after 60 minutes.

A nonwoven composite material which is particularly useful in the manufacture of surface webs for absorbent articles of hygiene has thus been produced according to the invention.

I claim:

1. A composite nonwoven material comprising:
   a layer made of a nonwoven material which is permeable to body fluids; and
   a sheet of carded synthetic fibers permeable to body fluids,
   said carded fiber sheet being bonded to the nonwoven layer solely by needling;
   wherein said composite material includes a first face and a second face and said carded fiber sheet and the nonwoven layer are bonded by needling from both the first face and the second face of said composite material.

2. The composite nonwoven material of claim 1, wherein the synthetic fibers of the carded sheet are chosen from the group consisting of polyester, polyethylene, polypropylene, nylon and ethylene-propylene copolymer fibers.

3. The complete nonwoven material of claim 1, wherein the nonwoven layer has a weight per unit area ranging from 10 to 30 g/m².

4. The composite nonwoven material of claim 1, wherein the sheet of carded synthetic fibers has a weight per unit area ranging from 20 to 60 g/m².

5. The composite nonwoven material of claim 1, wherein the sheet of carded synthetic fibers has a denier ranging from 3 to 13.

6. An absorbent article of hygiene comprising:
   an outer layer which is impervious to body fluids;
   an inner surface web which is permeable to body fluids and intended to come in contact with a user's body;
   an absorbent pad arranged between said outer layer and said inner surface web;
   a composite nonwoven material arranged between the inner surface web and the absorbent pad, the composite nonwoven material consisting of one layer made of a nonwoven material which is permeable to body fluids and a sheet of carded synthetic fibers permeable to body fluids, said carded fiber sheet bonded to the nonwoven layer solely by needling;
   wherein, the composite nonwoven material is arranged with the nonwoven layer in contact with the absorbent pad and the sheet of carded synthetic fibers in contact with said inner surface web; and
   wherein the composite nonwoven material includes a first face and a second face, said carded fiber sheet being bonded to the nonwoven layer by needling from both said first face and said second face of the composite nonwoven material.

7. The absorbent article of hygiene of claim 6, wherein the synthetic fibers of the carded sheet are chosen from the group consisting of polyester, polyethylene, polypropylene, nylon and ethylene-propylene copolymer fibers.

8. The absorbent article of hygiene of claim 6, wherein the nonwoven layer has a weight per unit area ranging from 10 to 30 g/m².

9. The absorbent article of hygiene of claim 6, wherein the sheet of carded synthetic fibers has a weight per unit area ranging from 20 to 60 g/m².

10. The absorbent article of hygiene of claim 6, wherein the sheet of carded synthetic fibers has a denier ranging from 3 to 13.

11. A composite nonwoven material consisting of:
    a layer made of a nonwoven material which is permeable to body fluid; and
    a sheet of carded synthetic fibers permeable to body fluids, said carded fiber sheet being bonded to the nonwoven layer solely by needling;
    wherein the nonwoven layer has a weight per unit area ranging from 10 to 30 g/m²; and
    wherein the sheet of carded synthetic fibers has a weight per unit area ranging from 20 to 60 g/m²;
    wherein the composite nonwoven material includes a first face and a second face, said carded fiber sheet being bonded to the nonwoven layer by needling from both said first face and said second face of the composite nonwoven material.

12. An absorbent article of hygiene comprising:
    an outer layer which is impervious to body fluids;

an inner surface web which is permeable to body fluids and intended to come in contact with a user's body;

an absorbent pad arranged between said outer layer and said inner surface web;

a composite nonwoven material arranged between the inner surface web and the absorbent pad, the composite nonwoven material consisting of one layer made of a nonwoven material which is permeable to body fluids and a sheet of carded synthetic fibers permeable to body fluids, said carded fiber sheet bonded to the nonwoven layer solely by needling;

wherein, the composite nonwoven material is arranged with the nonwoven layer in contact with the absorbent pad and the sheet of carded synthetic fibers in contact with said inner surface web; and wherein the nonwoven layer has a weight per unit area ranging from 10 to 30 g/m$^2$.

13. An absorbent article of hygiene comprising:

an outer layer which is impervious to body fluids;

an inner surface web which is permeable to body fluids and intended to come in contact with a user's body;

an absorbent pad arranged between said outer layer and said inner surface web;

a composite nonwoven material arranged between the inner surface web and the absorbent pad, the composite nonwoven material consisting of one layer made of a nonwoven material which is permeable to body fluids and a sheet of carded synthetic fibers permeable to body fluids, said carded fiber sheet bonded to the nonwoven layer solely by needling;

wherein, the composite nonwoven material is arranged with the nonwoven layer in contact with the absorbent pad and the sheet of carded synthetic fibers in contact with said inner surface web; and wherein the sheet of carded synthetic fibers has a weight per unit area ranging from 20 to 60 g/m$^2$.

* * * * *